(12) United States Patent
Bernardin et al.

(10) Patent No.: US 8,546,598 B2
(45) Date of Patent: Oct. 1, 2013

(54) SILANE COMPOUNDS HAVING A CYCLIC CARBON CHAIN INCLUDING AN ALKYNE FUNCTION FOR FUNCTIONALIZING SOLID SUBSTRATES AND IMMOBILIZING BIOLOGICAL MOLECULES ON SAID SUBSTRATES

(75) Inventors: Aude Bernardin, Lailly-en-Val (FR); Guillaume Delapierre, Vif (FR); Antoine Hoang, Grenoble (FR); Isabelle Texier-Nogues, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 23 days.

(21) Appl. No.: 13/257,326

(22) PCT Filed: Mar. 16, 2010

(86) PCT No.: PCT/FR2010/000218
§ 371 (c)(1),
(2), (4) Date: Dec. 19, 2011

(87) PCT Pub. No.: WO2010/106243
PCT Pub. Date: Sep. 23, 2010

(65) Prior Publication Data
US 2012/0095203 A1 Apr. 19, 2012

(30) Foreign Application Priority Data
Mar. 18, 2009 (FR) ..................................... 09 01254

(51) Int. Cl.
*C07F 7/04* (2006.01)
*C40B 60/00* (2006.01)
*C12M 1/34* (2006.01)

(52) U.S. Cl.
USPC ........................... 556/445; 506/37; 435/287.9

(58) Field of Classification Search
USPC ......................................................... 556/445
See application file for complete search history.

(56) References Cited

FOREIGN PATENT DOCUMENTS

EP 0 664 452 7/1995

OTHER PUBLICATIONS

U.S. Appl. No. 13/257,365, filed Nov. 2, 2011, Delapierre, et al.
International Search Report issued Jun. 14, 2010 in PCT/FR10/000218 filed Mar. 16, 2010.

*Primary Examiner* — Johann R Richter
*Assistant Examiner* — Kofi Adzamli
(74) *Attorney, Agent, or Firm* — Oblon, Spivak, McClelland, Maier & Neustadt, L.L.P.

(57) ABSTRACT

The invention relates to a silane compound including a cycloalkyne functionality, to a method for functionalising a solid substrate, and to the solid substrate thus produced. The silane compound of the invention corresponds to the formula X-E-A-Z where X is a silyl group, E is an organic spacer group, A is a single bond or a —CONH—, —NHCO—, —OCH$_2$CONH—, —NHCOCH$_2$O—, —O— or —S— group, and Z is a cycloalkyne or heterocycloalkyne with at least 8 members. The invention is particularly suitable for use in the field of medicine.

19 Claims, No Drawings

SILANE COMPOUNDS HAVING A CYCLIC CARBON CHAIN INCLUDING AN ALKYNE FUNCTION FOR FUNCTIONALIZING SOLID SUBSTRATES AND IMMOBILIZING BIOLOGICAL MOLECULES ON SAID SUBSTRATES

The invention relates to a silane compound comprising a cycloalkyne functionality.

It also relates to a process for the functionalization of a solid support and to the solid support thus obtained.

It also relates to a process for the immobilization of a biological molecule, to a process for sealing two solid supports and to the structure composed of the two sealed solid supports.

The analysis of the structure, of the arrangement and of the sequence, and also the study of the role, of a biological molecule of interest is of major importance in the prediction, diagnosis and treatment of diseases.

Supports carrying immobilized biological molecules, such as nucleic acids, proteins, sugars or lipids, are advantageously used for the detection and the recognition of biological entities, and for the study of the function thereof and the role thereof in the natural environment.

However, these supports carrying immobilized biological molecules have other applications, such as the separation and the purification of biological molecules.

The functionalized supports used in these applications have to have the following characteristics:
  to make possible the reproducible immobilization of the biological molecules of interest, and
  to make possible the immobilization of biological molecules of interest in a sensitive way, the sensitivity of a functionalized solid support depending on the degree of immobilization and on the method of detection of a signal but also on the level of background noise.

The immobilization of biological molecules of interest on supports is generally carried out in two stages:
  a first stage of functionalization of the supports, which consists of a chemical modification of their surface by the grafting of coupling agents which will provide for the attaching of the biological molecules to the support, and
  a second stage of immobilization, consisting in establishing an interaction between the biological molecules and the coupling agents grafted to the support, it being possible for the interaction to consist of the formation of a covalent bond between the biological molecule and the coupling agent or of weaker bonds (such as electrostatic or hydrophobic interactions).

The coupling agents are grafted to the surface of the supports by reaction of the hydroxyl functional groups of the support and of the reactive functional groups of the agent, to form covalent bonds between the coupling agent and the support.

Various grafting chemistries which make possible the coupling of biological molecules of interest to surfaces via coupling agents exist, but generally exhibit reactions which are not all compatible with a use in biology, without affecting the molecular entities to be grafted to this surface.

Furthermore, these reactions often involve chemical functional groups which may react non-specifically with undesired sites of the biological molecules of interest to be immobilized.

Furthermore, it is advantageous to be able to modify surfaces with living cells, bacteria or complex and delicate biomolecules, such as metalloenzymes, which require very mild coupling conditions as close as possible to the conditions of the living environment.

There exist rather few coupling reactions which can be used under the conditions of the living environment.

This is because such a coupling involves a number of constraints:
  none of the reactants or the reaction products must be toxic,
  the reactive products have to be chemically inert with regard to the functional groups of the molecular entity to be grafted in order to obtain better coupling specificity, and
  the reaction must take place rapidly in an aqueous medium, at physiological pH and physiological temperature, if possible, and must not depend on the concentration of salts present in the medium.

All these conditions make it impossible to employ reactions requiring the use of metal catalysts or surfactants suitable for the aqueous medium.

The metals are generally toxic, can interact with numerous biological molecules and can modify the functioning of the metalloenzymes or disrupt homeostasis.

Likewise, surfactants are commonly used to destroy cell walls.

There then remain few chemical reactions suitable for working on living tissues, in particular which make possible covalent grafting.

Among them, the cycloaddition reaction between an azide and an alkyne situated within a carbon ring is described in the patent application US 2006/0110782 A1. This reaction has the advantage of being carried out under mild conditions compatible with the biological world:
  a reaction at physiological temperature,
  a reaction in water, and
  no additive, such as a metal catalyst, ligand or base, is necessary.

In this context, the inventors set themselves the aim of providing novel silane compounds capable of being grafted to the surface of a solid support and comprising groups which make possible a cycloaddition reaction in order to immobilize biological entities of interest, such as living cells (eukaryotes or prokaryotes), biological molecules (nucleic acids, proteins, sugars, lipids) and any other sensitive molecule.

This cycloaddition reaction is carried out under conditions of the living environment, namely in water, at physiological temperature and in the absence of any other additive.

Thus, the invention provides a silane compound, characterized in that it has the following formula I:

X-E-A-Z          Formula I in which:
  X is a silyl group capable of creating a covalent bond after reaction with the hydroxyl functional groups of a support,
  E represents an organic spacer group,
  A represents a single bond or a group chosen from —CONH—, —NHCO—, —OCH$_2$CONH—, —NHCOCH$_2$O—, —O— or —S—, and
  Z represents a cycloalkyne or a heterocycloalkyne having at least 8 ring members of following formula Z:

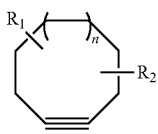

Formula Z in which $R_1$ and $R_2$ represent, independently of one another, H, $NO_2$, Cl, Br, F, I, OR, SR, $NR_2$, R, NHCOR, CONHR or COOR with R representing an alkyl or aryl group, $n \geq 1$, and, when Z is a heterocycloalkyne, the heteroatom is preferably O or S.

The preferred compounds of the invention are those in which, in the formula I, X is chosen from a trihalosilyl group, a trihydrosilyl group, a trialkoxysilyl group —$Si(OR_3)_3$ with $R_3$ representing a linear or branched alkyl group of 1 to 6 carbon atoms or a phenyl group; a triaminoalkylsilyl group —$Si(NR_4R_5)_3$ with $R_4$ and $R_5$ independently representing a saturated, linear or branched, alkyl group of 1 to 6 carbon atoms or a phenyl group, or an organometallic group.

Preferably, in the formula I, E represents a hydrocarbon group optionally comprising one or more unsaturations and/or one or more aromatic groups and/or one or more heteroatoms.

In this case, preferably, the hydrocarbon group comprises from 2 to 24 carbon atoms.

More preferably, the hydrocarbon group is an alkylene group comprising from 2 to 24 carbon atoms.

Other preferred compounds have the following formula II:

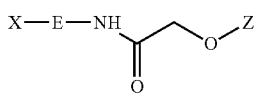

Formula II in which E represents an alkylene group comprising from 2 to 24 carbon atoms, X, Z, $R_1$ and $R_2$ being as defined above for the compounds of formula I.

Preferably, in the formula I, X is a triethoxysilyl group, E is a carbon chain comprising 3 carbon atoms, Z is a cyclooctyne, or a heterocyclooctyne, the alkyne triple bond of which is in the α position, the heteroatom of the heterocyclooctyne preferably being O or S, and $R_1$ and $R_2$ are hydrogen atoms, the compound having following formula III:

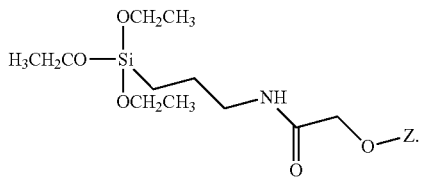

Formula III

The invention also provides a process for the functionalization of a solid support comprising hydroxyl functional groups at the surface, characterized in that it comprises a stage in which said support is brought into contact with a solution comprising at least one silane compound according to the invention and as defined in the above.

Preferably, the functionalization process of the invention comprises, before the stage of bringing into contact, a stage of treatment of the surface of the support in order to create, on said surface, the hydroxyl functional groups necessary for the grafting.

The solid support is an organic support or an inorganic support.

Preferably, the inorganic support is a metal oxide, silicon oxide, glass, metal or silicon.

Also preferably, the organic support is made of plastic, polyimide, polycarbonate or cycloolefin polymer (COP).

The invention also provides a solid support capable of being obtained by the functionalization process of the invention, characterized in that a compound according to the invention is bonded to the surface of the support via the X group of said compound.

The invention also provides a process for the immobilization of biological molecules on a solid support, characterized in that it comprises:
a) a stage in which the functionalization process according to the invention is employed, and
b) a stage in which the support obtained in stage a) is brought into contact with a solution comprising the biological molecule(s) to be immobilized.

Preferably, the biological molecule to be immobilized is chosen from nucleic acids, proteins, lipids, sugars, cells or bacteria.

However, the invention also provides a process for sealing two solid supports, characterized in that it comprises:
a) a stage in which a solid support comprising hydroxyl functional groups at the surface or a solid support comprising azide functional groups at the surface is brought into contact with a compound according to the invention, and
b) a stage in which the support obtained in stage a) is brought into contact with a solid support comprising azide functional groups at the surface, when the solid support obtained in stage a) comprises hydroxyl functional groups, or with a solid support comprising hydroxyl functional groups, when the support used in stage a) comprises azide functional groups at the surface.

Said solid supports can be supports made of a material chosen from a metal oxide, silicon oxide, glass, a metal or silicon.

Preferably, the solid supports are made of silicon.

The structure obtained by the sealing process of the invention is also a subject matter of the invention.

This structure is characterized in that it consists of two solid supports sealed together by a compound having the following formula IV:

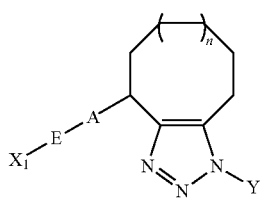

Formula IV in which E, A and n are as defined for the compounds of the invention, $X_1$ is a silyl group as defined for X for the compounds of the invention which has reacted with a hydroxyl functional group, Y is a covalent bond or an organic spacer.

Of course, the cycloalkene of the formula IV can comprise a heteroatom, preferably chosen between O and S, when the compound used for the sealing of the two supports is a heterocycloalkyne.

A better understanding of the invention will be obtained and other characteristics and advantages of the invention will become more clearly apparent on reading the explanatory description which follows.

The silane compounds of the invention are capable of being grafted to the surface of a solid support, this surface comprising hydroxyl functional groups.

In the invention, the term "surface comprising hydroxyl functional groups" is understood to mean a surface comprising predominantly hydroxyl functional groups or a surface comprising predominantly hydride functional groups but which is partially oxidized, this oxidation resulting in the formation of hydroxyl functional groups from the hydride functional groups.

The compounds of the invention have a first functionality which is a silyl group capable of creating a covalent bond after reaction with the hydroxyl functional groups of the support.

This silyl group makes possible the covalent attachment of the silane compound of the invention to the hydroxyl functional groups of the support.

The support can, for example, be a solid support made of silicon, indium tin oxide (ITO), titanium or plastic.

It can also be made of silicon oxide, glass or another metal.

The support can also be an organic support made of plastic, polyimide, polycarbonate or cycloolefin polymer (COP).

The silane compounds of the invention are also capable of entering into a cycloaddition reaction in order to immobilize biological entities of interest.

Thus, the silane compounds of the invention have a second functionality which is a cycloalkyne or a heterocycloalkyne of following formula Z:

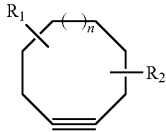

Formula Z

The cycloalkyne or, if appropriate, the heterocycloalkyne has at least 8 ring members. This is why, in the above formula Z, n is greater than or equal to 1.

When Z is a heterocycloalkyne, the heteroatom is preferably O or S.

It also comprises at least one triple-bonded unsaturation, that is to say an alkyne functional group, at any one of the positions inside the ring.

The functionality of above formula Z can also comprise substituents.

These substituents, denoted $R_1$ and $R_2$ in the above formula Z, represent, independently of one another, a hydrogen atom, a chlorine atom, a bromine atom, a fluorine atom, an iodine atom, an $NO_2$ group or also an OR, or SR, or $NR_2$, or R, or NHCOR, or CONHR, or COOR group, with R representing an alkyl or aryl group.

Preferably, $R_1$ and $R_2$ represent H.

The cycloaddition reaction to immobilize the biological entities of interest will take place with the alkyne functional group (triple bond).

More specifically, the two functionalities, that is to say the silyl group and the functionality of formula Z, are preferably separated from one another by a spacer group and/or a group chosen from —CONH—, —NHCO—, —OCH$_2$CONH—, —NHCOCH$_2$O—, —O— or —S—.

More specifically, the silane compounds of the invention have the following formula I:

X-E-A-Z    Formula I in which:
X is a silyl group capable of creating a covalent bond after reaction with the hydroxyl functional groups of a support,
E represents an organic spacer group,
A represents a single bond or a group chosen from —CONH—, —NHCO—, —OCH$_2$CONH—, —NHCOCH$_2$O—, —O— or —S—, and
Z represents a cycloalkyne or a heterocycloalkyne having at least 8 ring members of following formula Z:

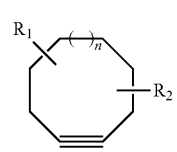

Formula Z in which $R_1$ and $R_2$ represent, independently of one another, H, $NO_2$, Cl, Br, F, I, OR, SR, $NR_2$, R, NHCOR, CONHR or COOR with R representing an alkyl or aryl group, and n≤1, and, when Z is a heterocycloalkyne, the heteroatom is preferably O or S.

In the formula I, X represents the silyl group capable of creating a covalent bond after reaction with the hydroxyl functional groups of a support.

As has already been said, the hydroxyl functional groups can also be obtained by the combination of hydride functional groups predominantly present at the surface of the support and a slight oxidation of the support.

This group X can, for example, be a trihalosilyl group, such as a trifluorosilyl group or a trichlorosilyl group, a trihydrosilyl group, a trialkoxysilyl group Si(OR$_4$)$_3$ with R$_4$ representing a saturated, linear or branched, alkyl group of 1 to 6 carbon atoms or a phenyl group, such as a trimethoxysilyl group, a triethoxysilyl group or a triisopropoxysilyl group, a triaminoalkylamino group —Si(NR$_5$R$_6$)$_3$ with R$_5$ and R$_6$ independently representing a saturated, linear or branched, alkyl group of 1 to 6 carbon atoms or a phenyl group, an organometallic group, such as an organomagnesium or organolithium group, or a hydrolyzable group.

In the formula I, the group E is an organic spacer group.

Its essential function is to confer specific properties on the film resulting from the grafting of the silane compounds to the surface of a support.

This group E is generally a hydrocarbon group preferably comprising from 2 to 24 carbon atoms and optionally comprising one or more unsaturations and/or one or more aromatic groups and/or one or more heteroatoms.

By way of example, the group E can be an alkylene group, that is to say a sequence of the —CH$_2$— type comprising, for example, from 8 to 24 carbon atoms.

Groups of this type confer, on the silane compounds, once grafted to a support, an ability to interact with one another, by creation of interchain interactions, and thus contributes to the achievement of organized monolayers on the surface of the support.

The group E can also be a fluoroalkylene group comprising from 3 to 24 carbon atoms.

These groups contribute to conferring, on the film resulting from the grafting of the silane compounds comprising them, properties which allow them to be used in chromatography and in electrophoresis.

However, the group E can be a hydrocarbon group comprising one or more unsaturations, such as a group of the alkene type.

An example of such a group is an alkylene group as defined above interrupted by one or more alkene unsaturations.

When the group E comprises at least two unsaturations, it confers on the silane compounds, once grafted to a support, an ability to crosslink.

The group E can also be a hydrocarbon group comprising one or more aromatic groups.

Mention may be made, for example, of a group comprising aromatic groups conjugated with linear unsaturated groups, such as a group resulting from the sequence of a phenylene-vinylene unit.

These groups contribute to conferring, on the film resulting from the grafting of the silane compounds comprising them, nonlinear optical properties.

The group E can also be a group comprising pyrrole or thiophene units.

These groups contribute to conferring, on the film resulting from the grafting of the silane compounds comprising them, electron conduction properties.

A preferred group is a group comprising one or more aromatic rings substituted by one or more aromatic groups, such as a group comprising a sequence of quinone units or of diazo units.

These groups contribute to conferring, on the film resulting from the grafting of the silane compounds comprising them, photo/electroluminescence properties.

A first family of silane compounds according to the invention is a family in which A is a group of formula —NHCOCH$_2$O—.

The compounds of this first preferred family of compounds of the invention have the following formula II:

$$X-E-NH\underset{O}{\overset{}{\diagdown}}\diagup^{O-Z} \qquad \text{Formula II}$$

in which X, E, R$_1$, R$_2$ and Z are as defined above.

The more particularly preferred compounds of the invention are those in which A is a group of formula —NHCOCH$_2$O— and E is an alkylene group comprising from 3 to 24 carbon atoms.

Preference is even more particularly given, in the invention, to the compounds in which A is —NHCOCH$_2$O—, E is an alkylene group comprising 3 carbons, X is an —Si(OCH$_2$CH$_3$)$_3$ group, Z is an 8-membered carbon ring, R$_1$ and R$_2$ are hydrogen atoms and the group A is bonded in the α position to the triple bond.

These very particularly preferred compounds of the invention have the following formula III:

$$\text{Formula III}$$

$$H_3CH_2CO-\underset{\underset{OCH_2CH_3}{|}}{\overset{\overset{OCH_2CH_3}{|}}{Si}}-\diagdown\diagup\diagdown NH\underset{O}{\overset{}{\diagdown}}\diagup^{O-Z}$$

These compounds make it possible to functionalize a solid support comprising hydroxyl functional groups at the surface.

The invention thus provides a process for the functionalization of a solid support comprising hydroxyl functional groups at the surface which comprises a stage in which a solution comprising at least one silane compound according to the invention is brought into contact with said support.

This process can comprise, beforehand, a stage of treatment of the surface of the support in order to create, on this surface, hydroxyl functional groups necessary for the grafting.

Of course, the invention also provides a solid support capable of being obtained by the functionalization process of the invention.

This solid support is characterized in that a compound according to the invention is bonded to the surface of the support via the silyl group of the compound of the invention.

The functionalization of a solid support with the compound according to the invention makes possible the immobilization of biological molecules on a solid support.

The invention thus provides a process for the immobilization of biological molecules on a solid support.

This immobilization process comprises a stage of implementation of the process for the functionalization of a solid support according to the invention and a stage in which the support thus obtained is brought into contact with a solution comprising the biological molecule(s) to be immobilized.

However, as will be clearly apparent to a person skilled in the art, it is also possible first of all to bring a compound according to the invention into contact with the molecule to be immobilized and then to carry out the process for the functionalization of a solid support according to the invention.

In both cases, the biological molecule to be immobilized is preferably chosen from nucleic acids, proteins, lipids, sugars, cells and bacteria.

Again, however, the compounds of the invention and the process for the functionalization of a solid support according to the invention also make it possible to seal two solid supports together.

The process for sealing two solid supports comprises a stage in which the process for the functionalization of a solid support according to the invention with a compound according to the invention is carried out and a stage in which the support thus obtained is brought into contact with a second solid support bonding at least one surface comprising azide functional groups.

The azide functional groups will then react with the triple bond of the group Z of the compounds of the invention.

However, here again, as will be clearly apparent to a person skilled in the art, the process for sealing two solid surfaces according to the invention can also comprise bringing a compound according to the invention into contact with a solid support having at least one surface comprising azide functional groups and only subsequently the stage of bringing the solid support comprising the compounds of the invention bonded to the azide functional groups of the first support into contact with a second support comprising at least one surface comprising hydroxyl functional groups, that is to say the functionalization process according to the invention.

In all cases, the solid supports can be organic or inorganic supports.

More particularly, they can be chosen from a metal oxide, silicon oxide, glass, a metal or silicon or also plastic, a polyimide, polycarbonate or a cycloolefin polymer.

The structure obtained by carrying out the process of sealing two solid supports of the invention is also a subject matter of the invention.

This structure consists of two solid supports sealed together by a compound of following formula IV:

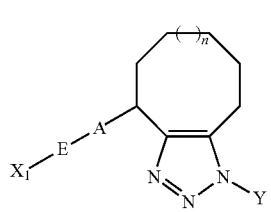

Formula IV in which E and A are as defined for the compounds of the invention, n is greater than or equal to 1, $X_1$ is a silyl group as defined for X for the compounds of the invention but which has reacted with a hydroxyl functional group, Y is a covalent bond or an organic spacer as defined for E, and the cycloalkene ring can comprise a heteroatom, preferably O or S.

In this structure, the first support is bonded to $X_1$ and the second support is bonded to Y.

The silane compounds of the invention can be synthesized by processes known to a person skilled in the art.

By way of example, in order to obtain compounds in which E is an alkylene group, A is —NHCOCH$_2$O— and X is an —Si(OR$_3$)$_3$ group, the preparation can be envisaged in two stages according to the following reaction scheme.

1) Reaction of a carboxyl compound carrying the carbon ring Z with an aminated alkene chain via the peptide coupling reaction in the presence of dicyclo-hexylcarbodiimide (DDC):

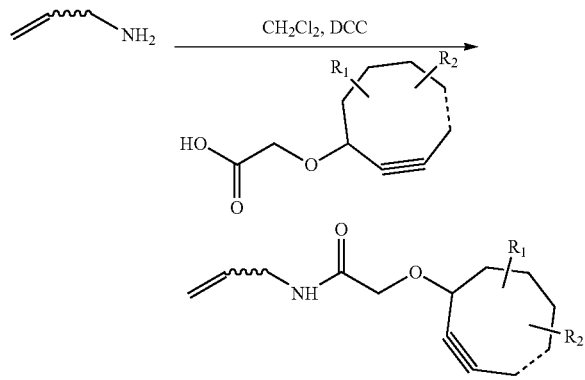

The wavy bond of the aminated alkene chain situated between the end carrying the double bond and the end carrying the NH$_2$ functional group represents a hydrocarbon group of variable length connecting the double bond to the NH$_2$ functional group.

2) The compounds obtained on conclusion of stage 1) are subsequently subjected to a hydrosilylation reaction with a reactant of the HSi(OR$_3$)$_3$ type, in the presence of a Karstedt catalyst Pt[Si(CH$_2$)$_2$HC=CH$_2$]$_2$O, according to the following reaction scheme:

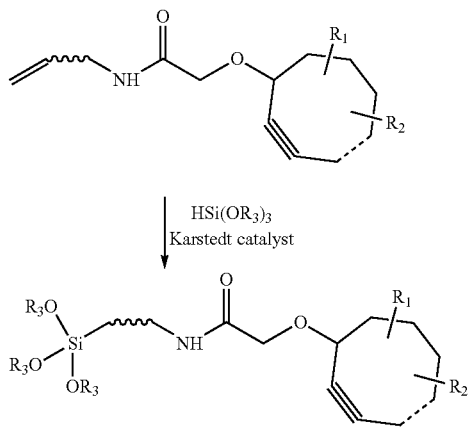

A person skilled in the art will adapt these synthetic schemes according to the silane compounds which he wishes to obtain.

As mentioned above, the silane compounds of the invention are capable of being grafted to the surface of a support, due to the presence of the X group, which is capable of reacting with hydroxyl functional groups present on the surface of the support to form covalent bonds.

Thus, the invention also relates to a process for the functionalization of a solid support comprising hydroxyl functional groups at the surface, comprising a stage in which a solution comprising at least one silane compound as defined above is brought into contact with said support.

This process can comprise, beforehand, a stage of treatment of the surface of the support in order to create, on said surface, the hydroxyl functional groups necessary for the grafting.

Thus, for a support made of silicon 1 0 0 (for example, of the wafer type), it is preferable, before functionalization, to treat the latter by bringing it into contact with a sodium hydroxide solution in order to generate silanol functional groups.

The supports which can be functionalized according to the process of the invention can be organic supports (for example made of plastics) or inorganic supports, for example supports made of metal oxide (for example, silica and its derivatives, such as glass or quartz, or indium tin oxide), metal supports (such as supports made of titanium) or supports made of silicon, the basic point being that these supports should be capable (optionally with the abovementioned pretreatment stage) of exhibiting hydroxyl functional groups at the surface for the grafting of the silane compounds of the invention.

Another subject matter of the invention is the functionalized solid support capable of being obtained by the process of the invention.

Because of the nature of the alkyne group present inside the ring carried by the silane compounds, which, once grafted to the surface of the support, have the ability to interact with biological molecules in order to immobilize them on the supports.

A subject matter of the present invention is thus a process for the immobilization of biological molecules on a functionalized solid support, comprising the following stages:

a) a stage of carrying out the process for the functionalization of the support as defined above;

b) a stage in which the support obtained in stage a) is brought into contact with a solution comprising the biological molecule(s) to be immobilized.

In order to make the invention better understood, an implementational example will be given thereof, purely by way of illustration and without implied limitation.

EXAMPLE 1

Synthesis of Cyclooctyne Silane

This compound is synthesized according to the following general scheme:

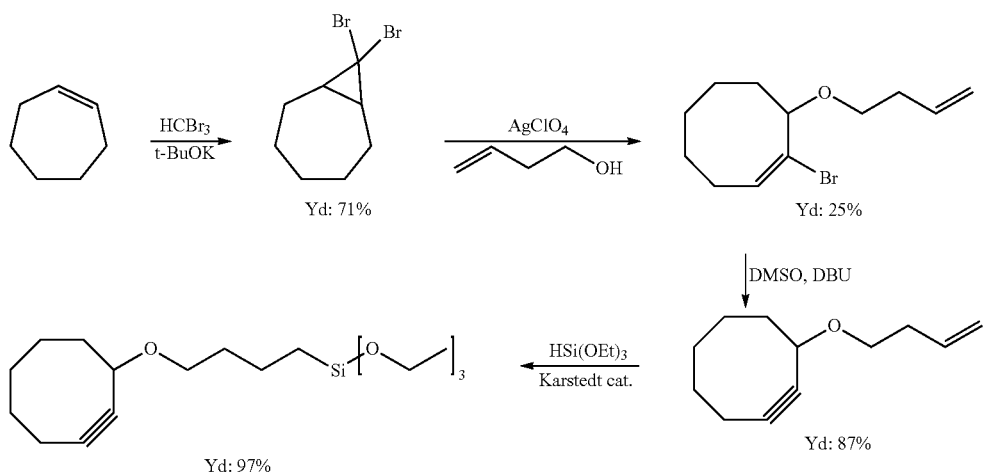

The vinyl functional group is incorporated by a nucleophilic substitution reaction between 8,8-dibromobicyclo[5.1.0]octane and 3-buten-1-ol.

The acetylene group is obtained by a debromination stage in dimethyl sulfoxide under hot conditions. The termination by the silane group takes place by a hydrosilylation.

Procedure and conditions of the reactions.

(1) 8,8-Dibromobicyclo[5.1.0]octane

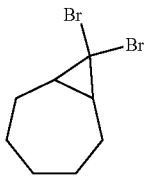

Cycloheptene (6.6 ml) and t-BuOK (12.56 g; 1.95 eq.) are dissolved in 100 ml of anhydrous pentane in a dry round-bottomed flask under argon. The cream yellow solution is vigorously stirred and placed in an ice/salt bath. Bromoform (7.3 ml, 1.46 eq.) is then added dropwise. The mixture is subsequently left to return to ambient temperature overnight, under argon and with vigorous stirring.

50 ml of water are added to this solution and the pH is neutralized with HCl (1M). The aqueous and organic phases are separated; the aqueous phase is extracted with 3×20 ml of cyclohexane and the organic phase is extracted with 3×20 ml of water. The organic phase is dried over MgSO$_4$, filtered and purified by flash chromatography (cyclohexane/AcOEt 95:5) to produce the compound 1 in the form of a colorless oil (10.77 g, 40.18 mmol, 71%) which is the desired 8,8-dibromobicyclo[5.1.0]octane.

$^1$H NMR (CDCl$_3$, 200 MHz) : δ (ppm) 1.05-1.22 (m, 3H) ; 1.34 (qq, J=1 and 7.5 Hz, 2H); 1.68 (ddd, J=1.5, 4 and 10.5 Hz, 2H); 1.76-1.92 (m, 3H); 2.23 (dtq, J=14, 6 and 1 Hz, 2H);

$^{13}$C NMR (CDCl$_3$, 200 MHz): δ (ppm) 40.7 (C$_8$ quat.); 34.8 (2, C$_{1,7}$) ; 32.2 (C$_4$) ; 28.9 (2, C$_{2,6}$) ; 27.9 (2, C$_{3,5}$).

(2) (E)-1-Bromo-8-(but-3-enyloxy)cyclooct-1-ene

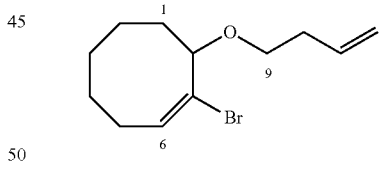

The compound 1 (2.73 g, 10.18 mmol) and 3-buten-1-ol (8.75 ml, 100.7 mmol, 10 eq.) are placed in anhydrous toluene (50 ml) in a round-bottomed flask wrapped in aluminum. AgClO$_4$ (6.33 g, 30.53 mmol, 3 eq.) is added and the suspension is stirred at ambient temperature for 48 h. After addition of 150 ml of AcOEt and filtering, the solution is washed with deionized water. The organic phase recovered is dried over MgSO$_4$, filtered and purified by flash chromatography (cyclohexane/AcOEt 99:1). The product 2 obtained (1.45 g, 5.59 mmol, 55%) is in the form of a yellow oil.

$^{13}$C NMR (CDCl$_3$, 200 MHz) : δ (ppm) 26.66; 28.56; 33.66; 34.46; 36.91 (C$_{1,5}$); 39.99 (C$_{10}$); 68.56 (C$_9$); 85.41 (C$_8$); 116.35 (C$_{12}$) ; 131.57 (C$_7$) ; 133.85 (C$_6$) ; 135.64 (C$_{11}$).

(3) 3-(But-3-enyloxy)cyclooct-1-yne

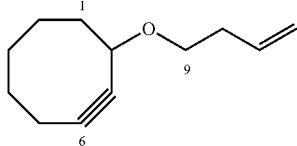

The compound 2 (2.04 g, 7.8 mmol) is dissolved in anhydrous DMSO (10 ml) and heated to 60° C. DBU (2.3 ml, 2 eq.) is added and the solution is stirred for 15 min. before adding further DBU (4.6 ml, 4 eq.) and again stirring for 15 min. Finally, DBU (4.6 ml, 4 eq.) is added a final time and the solution is stirred at 60° C. overnight and subsequently left to return to ambient temperature. 150 ml of AcOEt are added to this solution and extraction is carried out with HCl (1M). When the pH becomes basic, the organic phase is washed with water to neutrality. The extracted phase is dried over $MgSO_4$, filtered and purified by flash chromatography (cyclohexane/AcOEt 99:1) in order to produce the compound 3 (1.22 g, 6.8 mmol, 87%), a colorless liquid.

$^1$H NMR ($CDCl_2$, 200 MHz) : δ (ppm) 1.20-2.3 (m, 10H) ; 2.39 (dd, $J_{10\text{-}10'}$=6.67 Hz, 2H, $H_{10}$) ; 3.4 (d, $J_{9\text{-}9'}$=51.81 Hz, 2H, $H_9$) ; 4.2 (m, 1H, $H_8$) ; 5.08 (m, $J_{12\text{-}12'}$=11.44 Hz, 2H, $H_{12}$) ; 5.84 (m, 1H, $H_{11}$), $^{13}$C NMR ($CDCl_2$, 200 MHz) : δ (ppm) 20.6; 23.5; 26.4; 29.7 ($C_{2, 5}$) ; 34.3 ($C_{10}$) ; 42.2 ($C_1$) ; 68.5 ($C_9$) ; 72.3 ($C_8$); 93 ($C_7$) ; 99.8 ($C_6$) ; 116.2 ($C_{11}$) ; 135.2 ($C_{12}$).

(4) (4-(Cyclooct-2-ynyloxy)butyl)triethoxysilane

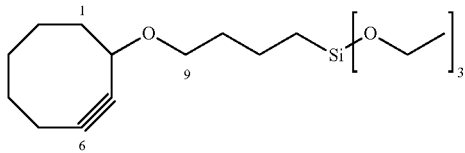

The compound 3 (1.28 g, 7.18 mmol) is mixed with triethoxysilane (3.6 ml). The Karstedt catalyst is added very slowly in a catalytic amount (10 drops). The reaction takes place at 45° C. over three days. The product is purified by flash chromatography (100% AcOEt) to give a brown liquid (2.4 g, 7 mmol, 97%).

$^1$H NMR ($CDCl_3$, 200 MHz) : δ (ppm) 1.4 and 2 (m, 10H); 3.54 (m, $J_{9\text{-}9'}$=39.1 Hz, 2H, $H_9$); 4.31 (m, 1H, $H_8$), $^{13}$C NMR ($CDCl_3$, 200 MHz) : δ (ppm) 14.6 ($C_{12}$) ; 18; 20; 26.5; 27.2; 34.1 ($C_{1, 5}$); 58.6 ($C_{13}$×3); 79 ($C_8$).

EXAMPLE 2

Grafting of the Compound of Example 1

Surface silanization protocol ($Si/SiO_2$):

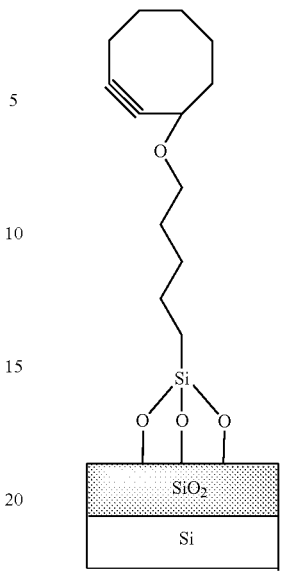

1) Rehydration by the Brown method: solution of NaOH in a mixture of deionized water (DW)/EtOH with stirring for 2h 00, followed by rinsing with DW.
2) Silanization: solution of silane in trichloro-ethylene overnight at ambient temperature, followed by rinsing with trichloroethylene, chloroform and EtOH under ultrasound.
3) Crosslinking: heating at 120° C. for 3 h 00.

EXAMPLE 3

Immobilization of Molecules by Click Chemistry on the Surface via the Silane

In order to demonstrate the "click" reaction on the modified support obtained in example 2, it was decided to carry out a "click" reaction between the cyclooctyne functional group at the surface and the azide group of a mannose ($N_3$-modified acetylated mannose) of formula:

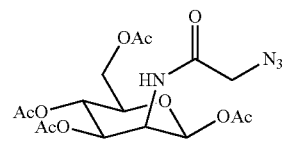 [SMILES: CC(=O)OCC1OC(OC(C)=O)C(NC(=O)CN=[N+]=[N-])C(OC(C)=O)C1OC(C)=O]

This mannose was chosen because it exhibits numerous C=O bonds.

A trace of mannose can be detected on the spectrum of the silane; this is because a band at 1750 cm$^{-1}$, which is characteristic of the C=O bond, is made out.

The invention claimed is:
1. A silane compound of formula (I):

$$X\text{-}E\text{-}A\text{-}Z, \quad (I)$$

wherein
X is a silyl group capable of creating a covalent bond after reaction with at least one hydroxyl functional group of a support,
E represents an organic spacer group, A represents a single bond or a group selected from the group consisting of —CONH—, —NHCO—, —OCH₂CONH—, —NHCOCH₂O—, —O—, and —S—, and Z represents a cycloalkyne or a heterocycloalkyne, comprising at least 8 ring members, of formula (Z):

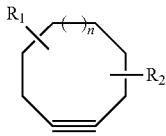

wherein

R₁ and R₂ represent, independently of one another, H, NO₂, Cl, Br, F, I, OR, SR, NR₂, R, NHCOR, CONHR, or COOR with R representing an alkyl or aryl group, n≥1 when Z is a heterocycloalkyne, the heteroatom is O or S.

2. The compound of claim 1 wherein, in formula (I), X is selected from the group consisting of a trihalosilyl group, a trihydrosilyl group, a trialkoxysilyl group —Si(OR₃)₃ with R₃ representing a linear or branched alkyl group of 1 to 6 carbon atoms or a phenyl group, and a triaminoalkylsilyl group —Si(NR₄R₅)₃ with R₄ and R₅ representing, independently of one another, a saturated, linear or branched, alkyl group of 1 to 6 carbon atoms or a phenyl group, or an organometallic group.

3. The compound of claim 1, wherein, in formula (I), E represents a hydrocarbon group optionally comprising an unsaturation, an aromatic group, or a heteroatom.

4. The compound of claim 3, wherein the hydrocarbon group comprises from 2 to 24 carbon atoms.

5. The compound of claim 4, wherein the hydrocarbon group is an alkylene group comprising from 2 to 24 carbon atoms.

6. The compound of claim 1, having formula (II):

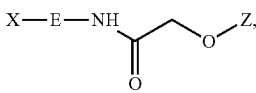

wherein E represents an alkylene group comprising from 2 to 24 carbon atoms.

7. The compound of claim 1, wherein, in formula (I),

X is a triethoxysilyl group,

E is a carbon chain comprising 3 carbon atoms,

Z is a cyclooctyne or a heterocyclooctyne, the alkyne triple bond of which is in the α position, and R₁ and R₂ are hydrogen atoms, the compound having formula (III):

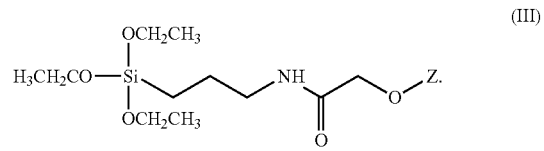

8. A process for functionalizing a solid support comprising at least one hydroxyl functional group on a surface, the process comprising:

contacting the solid support with a solution comprising at least one silane compound of claim 1.

9. The process of claim 8, further comprising, before the contacting:

treating the surface of the support in order to create, on the surface, the at least one hydroxyl functional group necessary for grafting.

10. The process of claim 8, wherein the solid support is an organic support or an inorganic support.

11. The process of claim 10, wherein the inorganic support is present and is a metal oxide, silicon oxide, glass, metal, or silicon.

12. The process of claim 10, wherein the organic support comprises plastic, polyimide, polycarbonate, or cycloolefin polymer (COP).

13. A solid support, obtained by the process of claim 8, wherein the compound of formula (I) is bonded to the surface of the support via the X group of the compound of formula (I).

14. A process for immobilizing at least one biological molecule on a solid support, the process comprising:

contacting a support obtained by the process of claim 8 with a solution comprising the at least one biological molecule to be immobilized.

15. The process of claim 14, wherein the biological molecule is at least one selected from the group consisting of a nucleic acid, a protein, a lipid, a sugar, a cell, or a bacteria.

16. A process for sealing two solid supports, comprising:

a) contacting a first solid support comprising at least one azide functional group on a surface with at least one compound of claim 1, to obtain a second solid support; and b) contacting the second support obtained in a) with a third solid support comprising at least one azide functional group on a surface, when the second solid support obtained in a) comprises hydroxyl functional groups, or with a solid support comprising at least one hydroxyl functional group, when the support employed in stage a) comprises at least one azide functional group on the surface.

17. The process of claim 16, wherein solid supports comprise at least one material selected from the group consisting of a metal oxide, silicon oxide, glass, a metal, or silicon.

18. The process of claim 16, wherein the solid supports comprise silicon.

19. The compound of claim 1, wherein Z is a heterocycloalkyne, and the heteroatom is O or S.

* * * * *